United States Patent [19]

Bühler et al.

[11] 4,154,739

[45] May 15, 1979

[54] 3-OXOBENZOTHIOPHENYL-IDENYL, HALO-ACETIC ACIDS

[75] Inventors: Niklaus Bühler, Rheinfelden; Hans Bosshard, Basel, both of Switzerland

[73] Assignee: Ciba-Geigy Corporation, Ardsley, N.Y.

[21] Appl. No.: 876,378

[22] Filed: Feb. 9, 1978

[30] Foreign Application Priority Data

Feb. 11, 1977 [LU] Luxembourg ............................ 76757

[51] Int. Cl.$^2$ ............................................ C07D 333/64
[52] U.S. Cl. .......................... 260/330.5; 260/306.7 R; 260/307 FA; 260/326.34; 544/54; 544/58; 544/96; 544/146; 544/333; 544/376; 548/300; 546/202
[58] Field of Search ......... 260/330.5, 293.57, 306.7 R, 260/307 FA; 326.34; 544/54, 58, 96, 146, 333, 376; 548/300

[56] References Cited

U.S. PATENT DOCUMENTS 3,816,467  6/1974  Wright ............................ 260/346.71

OTHER PUBLICATIONS

Mostoslavskii et al., Zh. Obshch. Khim. 32, 660, (1962).

*Primary Examiner*—Natalie Trousof
*Assistant Examiner*—Bernard Dentz
*Attorney, Agent, or Firm*—Luther A. R. Hall

[57] ABSTRACT

Novel halogeno-benzothiophenecarboxylic acids and a novel process for their preparation by reacting substituted or unsubstituted thiophenols with dihalogenomaleic anhydrides or derivatives thereof are described. The novel halogeno-benzothiophenecarboxylic acids are valuable intermediates for the preparation of pharmaceutical active compounds having an antiallergic action.

10 Claims, No Drawings

3-OXOBENZOTHIOPHENYL-IDENYL, HALO-ACETIC ACIDS

The present invention relates to novel halogeno-benzothiophene-carboxylic acids and a novel process for their preparation.

The novel halogeno-benzothiophene-carboxylic acids are of the formula I

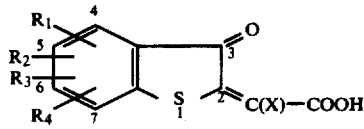

in which X is chlorine, bromine or fluorine, $R_1$ and $R_2$ independently of one another are hydrogen or a lower alkyl group, $R_3$ is hydrogen, a halogen atom or a hydroxyl or lower alkyl group and $R_4$ is hydrogen, a halogen atom, a hydroxyl, carboxyl, lower alkyl, lower alkoxy, phenoxy, cycloalkyl or acyl group or a substituted or unsubstituted amino group, or, if $R_3$ and $R_4$ are hydrogen, $R_1$ and $R_2$ together with the bonding C atoms in the ortho-position form a cycloalkyl group or a fused benzene ring.

The compounds according to the invention can be in the form of the cis or the trans isomers or in the form of mixtures of cis/trans isomers relative to the exocyclic C=C double bond. Mixtures of isomers of this type can be separated into their constituents on the basis of the differences in the physicochemical properties, in a conventional manner, for example by chromatography or by fractional crystallisation.

The compounds of the formula I can be prepared in a simple manner using readily accessible and comparatively inexpensive starting materials and in good to very good yields, by reacting a compound of the formula II

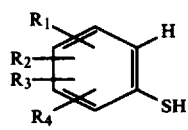

with a compound of the formula III

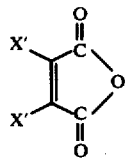

to give a compound of the formula IV

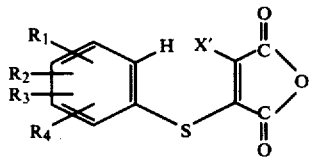

and subsequently converting the compound of the formula IV in the presence of a Lewis acid to a compound of the formula I.

In the above formulae II-IV, $R_1$, $R_2$, $R_3$ and $R_4$ are as defined under formula I and the two X' in formulae III and IV independently of one another are chlorine, bromine or fluorine.

In formula I X is preferably bromine and especially chlorine.

Lower alkyl or lower alkoxy groups as $R_1$ to $R_4$ have in particular 1–7 and preferably 1–4 carbon atoms, such as the methyl, ethyl, n-propyl, isopropyl, n-butyl, n-pentyl, n-heptyl, methoxy, ethoxy, n-propoxy, isopropoxy, n-butoxy, tert.-butoxy, n-pentyloxy and n-hexyloxy group. Particularly preferred lower alkyl and lower alkoxy groups have 1 to 2 carbon atoms, in particular the methyl group and the methoxy group.

If $R_3$ or $R_4$ is a halogen atom, this is, for example, a fluorine atom, but especially a bromine or chlorine atom.

Fused benzene rings formed by $R_1$ and $R_2$ together with bonding C atoms can be unsubstituted or substituted, for example by halogen atoms, in particular chlorine, or alkyl groups, especially those having 1 or 2 carbon atoms.

Preferably, however, $R_1$ and $R_2$ in formula I, together with the bonding C atoms, form an unsubstituted benzene ring bonded in the 4,5-position.

If, when $R_3$ and $R_4$=H, $R_1$ and $R_2$ together with the bonding C atoms in the ortho-position form a cycloalkyl group, this has, in particular, 5–7 ring members and can be substituted, for example by alkyl groups having 1–4 and especially 1 or 2 carbon atoms. Preferably, however, cycloalkyl groups of this type are unsubstituted and bonded in the 5,6-position of the benzothiophene; in particular, $R_1$ and $R_2$ together with the bonding C atoms form a cyclopentane or cyclohexane ring bonded in the 5,6-position.

Preferred cycloalkyl groups $R_4$ are unsubstituted cycloalkyl groups having 5 to 8 ring carbon atoms, such as the cyclopentyl, cycloheptyl and cyclooctyl group and in particular the cyclohexyl group.

Phenoxy groups $R_4$ are preferably unsubstituted but can also be substituted by alkyl or alkoxy groups having 1–4 and especially 1 or 2 carbon atoms, such as the methyl or methoxy group, or by halogen atoms, for example chlorine.

Acyl groups $R_4$ are derived, for example, from aliphatic, carbocyclic-aromatic or heterocyclic-aromatic carboxylic acids. In particular they are aroyl and alkanoyl groups, for example benzoyl groups, which can be substituted by alkyl or alkoxy groups having 1–4 and especially 1 or 2 carbon atoms or by halogen atoms, such as chlorine, but are preferably unsubstituted, or -CO-alkyl groups having 1–6 and especially 1–3 carbon atoms in the alkyl part, such as the acetyl, propionyl, butyryl, valeroyl and pivaloyl group.

If $R_4$ is a substituted amino group, possible groups are, in particular, those of the formulae

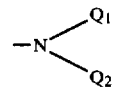

and —NHCO—$Q_3$, in which $Q_3$ is lower alkyl, $Q_1$ is hydrogen or lower alkyl and $Q_2$ is lower alkyl, or $Q_1$ and $Q_2$ together are alkylene having 4–7 carbon atoms, which can be interrupted by —S—, —O— or

in which $Q_4$ is hydrogen or lower alkyl. Lower alkyl groups as $Q_1$ to $Q_4$ have in particular 1–6 and preferably 1–4 carbon atoms. Particularly preferentially, $Q_1$, $Q_2$ or $Q_3$ are methyl or ethyl, or $Q_1$ and $Q_2$ together are the grouping —(CH$_2$)$_4$—, —(CH$_2$)$_5$—, —(CH$_2$)$_2$O(CH$_2$)$_2$— or

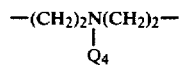

and $Q_4$ is hydrogen or methyl.

If one of $R_1$ to $R_4$ is hydrogen, the remaining substituents in the compounds of the formula I are preferably in the 5-, 6- and/or 7-position. According to a further preference, two of the substituents $R_1$ to $R_4$ are hydrogen and the remaining substituents are in the said preferred positions, especially in the 5- and/or 6-position.

Preferred compounds of the formula I are those in which X is chlorine, $R_1$ and $R_2$ independently of one another are hydrogen or an alkyl group having 1–4 and especially 1 or 2 carbon atoms, $R_3$ is hydrogen, chlorine, fluorine, bromine or an alkyl group having 1–4 and especially 1 or 2 carbon atoms and $R_4$ is hydrogen, chlorine, fluorine, bromine, —OH, —COOH, cyclohexyl, an alkyl or alkoxy group having 1–4 and in particular 1 or 2 carbon atoms, an alkanoyl group having 2–7 carbon atoms, for example acetyl, an alkanoylamino group having 2–4 carbon atoms, for example acetylamino, or a N,N-dialkylamino group having 1 or 2 carbon atoms in each alkyl part.

Further preferred compounds of the formula I are those in which X is chlorine, $R_3$ and $R_4$ are hydrogen and $R_1$ and $R_2$ together are an alkylene group having 3–5 carbon atoms, which is bonded in the 5,6-position, or a 1,4-butadienyl group bonded in the 4,5-position.

Particularly preferred compounds are those of the formula Ia

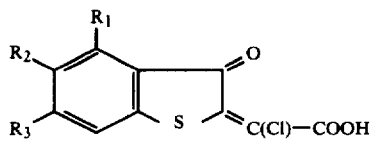

in which $R_1$ and $R_2$ independently of one another are hydrogen or alkyl having 1–4 carbon atoms, such as methyl, and $R_3$ is hydrogen, alkyl or alkoxy having 1–4 carbon atoms, such as methyl and methoxy, or —OH, or in which $R_1$ and $R_2$ together form 1,4-butadienylene and $R_3$ is hydrogen, or $R_1$ is hydrogen and $R_2$ and $R_3$ together form alkylene having 3 or 4 carbon atoms, for example 1,3-propylene.

Very particularly preferred compounds are those of the formula Ia in which $R_1$ is hydrogen or methyl and one of the radicals $R_2$ and $R_3$ is methyl and the other is hydrogen or methyl, or in which $R_1$ is hydrogen and $R_2$ and $R_3$ together are trimethylene.

The starting materials of the formula II and III are known per se or can be prepared by conventional methods. Compounds of the formula III which are preferably used are those in which the two X' have the same meaning, in particular dichloromaleic anhydride.

The reaction of the compound of the formula II with a compound of the formula III is advantageously carried out in the presence of an inert organic solvent and if desired with the addition of an organic or inorganic base. The reaction is preferably carried out with the addition of a base according to the definition.

The compound of the formula III is appropriately employed in an approximately 1- to 10-fold molar amount; the organic or inorganic base is generally used in substantially stoichiometric amounts or in a slight excess (up to about 1.5 times the molar amount).

The reaction temperatures are generally between about 0° and 120° C. and preferably between about 20° and 70° C.

Suitable inert organic solvents for the reaction mentioned are, for example, aliphatic and aromatic hydrocarbons, which may or may not be chlorinated, such as methylene chloride, 1,2-dichloroethane, 1,1,2,2-tetrachloroethane, benzene, toluene, chlorobenzene and nitrobenzene; aliphatic and cyclic ethers, such as diethyl ether, tetrahydrofurane and dioxane; ethylene glycol monoalkyl ethers and dialkyl ethers having 1–4 carbon atoms in each alkyl part, such as ethylene glycol monomethyl ether and ethylene glycol monoethyl ether, ethylene glycol dimethyl ether and ethylene glycol diethyl ether; aliphatic monocarboxylic acids having 1–4 carbon atoms in the alkyl part and alkyl esters of aliphatic monocarboxylic acids having a total of 2–6 carbon atoms, such as acetic acid, propionic acid and butyric acid and methyl, ethyl and butyl formate or methyl, ethyl and butyl acetate; cyclic amides, such as N-methyl-2-pyrrolidone, N-acetyl-2-pyrrolidone and N-methyl-ϵ-caprolactam; N,N-dialkylamides of aliphatic monocarboxylic acids having 1–3 carbon atoms in the acid part, such as N,N-dimethylformamide, N,N-dimethylacetamide, N,N-diethylacetamide and N,N-dimethylmethoxyacetamide; tetrahydrothiophene dioxide (sulpholane) and dialkylsulphoxides, such as dimethylsulphoxide and diethylsulphoxide; aliphatic and cycloaliphatic ketones, such as acetone, methyl ethyl ketone, cyclopentanone and cyclohexanone.

Examples of organic and inorganic bases which can also be used in the reaction are tertiary amines, such as triethylamine, pyridine, pyridine bases or alkali metal acetates and alkaline earth metal acetates. Alkali metal acetates are preferred, especially sodium acetate and potassium acetate.

The intermediates of the formula IV are in general obtained in the form of viscous oils which solidify on cooling and can be isolated, and purified, in a conventional manner, for example by recrystallisation. However, isolation and purification of this type is not necessary.

The treatment (cyclisation) of the intermediates of the formula IV with a Lewis acid can be carried out in an inert organic solvent or in the melt. Examples of Lewis acids which can be used are: aluminium chloride, aluminium bromide, zinc chloride, tin tetrachloride, boron trifluoride, iron-III chloride, titanium tetrachloride, phosphorus trichloride, phosphorus oxychloride, antimony pentafluoride and antimony pentachloride. Aluminium chloride is preferably used.

The Lewis acid is appropriately employed in excess, for example in about 2 times to 10 times the molar amount.

Suitable organic solvents for the cyclisation are, for example: chlorinated aliphatic or aromatic hydrocarbons, such as methylene chloride, 1,2-dichloroethane, 1,2,3-trichloropropane, 1,1,2,2-tetrachloroethane and o-dichlorobenzene; n-pentane and n-hexane; nitromethane, nitrobenzene and carbon disulphide.

The cyclisation in the melt is appropriately carried out in the presence of low-melting salt mixtures, for example mixtures of aluminium chloride with inorganic or organic salts, such as ammonium halides, alkaline earth metal halides and alkali metal halides, for example ammonium chloride, magnesium chloride and calcium chloride, but especially sodium chloride and potassium chloride, and also pyridinium salts, for example N-alkylpyridinium halides. Eutectic salt mixtures, especially mixtures of aluminium chloride and sodium chloride and/or potassium chloride, are preferred. However, in themselves any desired salt mixtures can be employed if an adequate lowering of the melting point is achieved therewith.

However, the cyclisation is preferably carried out in an inert organic solvent, especially methylene chloride, 1,2-dichloroethane or 1,1,2,2-tetrachloroethane, or, alternatively, in the melt with the addition of sodium chloride and/or potassium chloride.

The cyclisation of the compounds of the formula IV to compounds of the formula I with the elimination of HX' is generally carried out at temperatures of between about 0° and 130° C. Temperatures of between about 0° and 90° C. are preferred for the cyclisation in the presence of an inert organic solvent, depending on the nature of the solvent. In most cases, however, the cyclisation in the presence of an inert organic solvent can already be carried out at temperatures of between about 0° and 40° C.

Temperatures of between about 70° and 120° C. are preferred for the cyclisation in the melt.

After the reaction has ended, the compounds of the formula I can be isolated in a conventional manner, for example by pouring the reaction mixture into a water-/ice mixture or by adding a dilute mineral acid, such as hydrochloric acid, filtering and washing with water. The compounds of the formula I obtained by the process according to the invention in general contain only slight impurities and can be used direct for preparative purposes. If desired, they can be converted to the analytically pure form by recrystallisation from suitable solvents, such as acetic acid, ethyl acetate, cellosolve, ethylene glycol dimethyl ether or ethylene glycol diethyl ether, acetone, methanol or ethanol, or by suspending in one of these solvents and filtering off.

The compounds of the formula I are obtained in the form of yellow to red crystals and are valuable intermediates for the preparation of pharmaceutical active compounds having an antiallergic action, for example 3-hydroxy-benzothienyl-2-glyoxylic acids and esters or salts thereof. The preparation of several pharmaceutical active compounds which have antiallergic properties and can be used, for example, for the treatment and prophylaxis of allergic diseases, such as asthma, hay fever, conjunctivitis, urticaria and eczema, is described in the examples.

EXAMPLES 1

66.8 g (0.4 mol) of dichloromaleic anhydride and 23.5 g (0.22 mol) of anhydrous sodium acetate in 300 ml of ethylene glycol dimethyl ether are initially introduced into a stirred flask. 24.8 g (0.2 mol) of p-thiocresol in 300 ml of ethylene glycol dimethyl ether are added dropwise at 50° C. in the course of 2 hours. During this period the temperature is raised stepwise to 70° C. The reaction mixture is then stirred for 16 hours at 70° C. The sodium chloride which has precipitated is separated off and the filtrate is evaporated. A viscous red oil is obtained. This is added dropwise in the course of 1.5 hours to a suspension, which is cooled to 0°–10° C. by means of an icebath, of 100 g (0.76 mol) of aluminium chloride in 100 ml of 1,2-dichloroethane. After stirring for one hour at 20°–25° C., the reaction mixture is poured onto 800 g of ice, the aqueous phase is decanted off and 50 ml of ethyl acetate are added to the resulting red oily product, whereupon crystallisation starts. After stirring for 1.5 hours, the orange-red crystals are separated off and dried at 60° C./100 mm Hg. This gives 38.1 g (75% of theory) of crystals which according to the thin layer chromatogram contain only insignificant amounts of impurities and can be used for further reactions without additional purification.

If further purification is desired, the crystals are suspended in 190 ml of ethyl acetate, the resulting mixture is heated to the boil and immediately cooled again and the product is filtered off with suction. After drying, 31.0 g of red crystals having a melting point of 176°–178° C. are obtained. According to the thin layer chromatogram, the purified product contains virtually no impurities.

NMR spectrum (100 Megahertz [MHz], δ values in ppm, solution in DMSO-d₆): 2.4 (s, 3H, CH₃), 7.4–8.0 (m, 3H, aromatic), 10.3 (s, broad, 1H, COOH, disappears on the addition of D₂O).

The spectroscopic findings from NMR, IR and MS and also the elementary analysis correspond to the formula

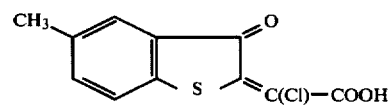

[2-chlorocarboxymethylene-5-methyl-[2H]-benzothiophen-3-one].

The chlorocarboxymethylene-benzothiophenones listed in the Table which follows were prepared in an analogous manner.

Table

| Ex. No. | Compound of the formula II | X—CO / X—CO | Solvent* | Reaction Time Hours* | Reaction Temp. °C. | Compound of the formula I | Yield % of theory | Melting point °C. |
|---|---|---|---|---|---|---|---|---|
| 2 | 4-chlorothiophenol | X = Cl | ClCH₂CH₂Cl | 1 | 20–25 | 2-chlorocarboxymethylene-5-chloro-[2H]-benzothiophen-3-one | 53.8 | >210 |
| 3 | thiophenol | " | " | 20 | " | 2-chlorocarboxymethylene-[2H]-benzothiophen-3-one | 77.5 | 157–59 (decomposition) |
| 4 | m-thiocresol | " | " | 1 | " | 2-chlorocarboxymethylene-6-methyl-[2H]benzothiophen-3-one | 90.3 | 214–16 (decomposition) |

Table-continued

| Ex. No. | Compound of the formula II | X...CO / X CO (X, X) | Solvent* | Reaction Time Hours* | Reaction Temp. °C. | Compound of the formula I | Yield % of theory | Melting point °C. |
|---|---|---|---|---|---|---|---|---|
| 5 | 3,4-dimethyl-thiophenol | " | " | 20 | " | 2-chlorocarboxymethylene-5,6j-dimethyl[2H]benzothiophen-3-one | 98 | about 205 (decomposition) |
| 6 | 2,5-dimethyl-thiophenol | " | " | 4 | " | 2-chlorocarboxymethylene-4,7-dimethyl[2H]benzothiophen-3-one | 85.4 | 180–84 (decomposition) |
| 7 | 4-acetylamino-thiopheol | " | " | 6.5 | 40 | 2-chlorocarboxymethylene-5-acetyl-amino[2H]benzothiophen-3-one | 67 | >210 |
| 8 | 2,4-dimethyl-thiophenol | " | " | 4 | 20–25 | 2-chlorocarboxymethylene-5,7-dimethyl[2H]benzothiophen-3-one | 80.2 | 192–93 (deomposition) |
| 9 | 3-methylmercapto-thiophenol | " | " | 1 | 40 | 2-chlorocarboxymethylene-6-methyl-mercapto[2H]benzothiophen-3-one | | >250 |
| 10 | 4-n-butyl-thiophenol | " | " | 3 | 20–25 | 2-chlorocarboxymethylene-5-n-butyl-[2H]benzothiophen-3-one | 45.3 | 120–24 |
| 11 | 2,5-dichloro-thiophenol | " | " | 20 | 20–25 | 2-chlorocarboxymethylene-4,7-dichloro-[2H]benzothiophen-3-one | 25.8 | >250 |
| 12 | p-thiocresol | X = Br | " | " | " | 2-bromocarboxymethylene-5-methyl-[2H]-benzothiophen-3-one | 47.1 | >250 |
| 13 | 3,4-trimethylene-thiophenol | Cl | " | 48 | 20–25 | 2-chlorocarboxymethylene-5,6-trimethylene-[2H]benzothiophene 3-one | 85.7 | >250 |

*for the cyclisation of the compound of the formula IV to the compound of the formula I.

EXAMPLE 14

24.4 g (0.095 mol) of the 2-chlorocarboxymethylene-5-methyl[2H]benzothiophen-3-one prepared according to Example 1 in 213 ml of 10% strength methanolic sulphuric acid are heated to the boil for 2 hours. After cooling, the resulting orange crystals are filtered off with suction and washed twice with, in each case, 125 ml of a saturated solution of sodium bicarbonate and once with 100 ml of water. After drying at 60° C./100 mm Hg, 18.2 g of 2-methoxycarbonylchloromethylene-5-methyl[2H]benzothiophen-3-one result in the form of red crystals; melting point 208° C. A further 2.3 g of crystals can be obtained from the mother liquor and the thin layer chromatogram of these crystals corresponds to that of the first crystalline product. Total yield=20.5 g or 79.7% of theory.

2-Methoxycarbonylchloromethylene-5,6-trimethylene[2H]-benzothiophen-3-one (melting point 197°–199° C., recrystallised from ethyl acetate) can be obtained in an analogous manner starting from 2-chlorocarboxymethylene-5,6-trimethylene[2H]-benzothiophen-3-one by treatment with methanolic sulphuric acid.

2-Methoxycarbonylchloromethylene-5-methyl[2H-]benzothiophen-3-one can also be prepared as follows:

7.6 g (0.03 mol) of 2-chlorocarboxymethylene-5-methyl-[2H]benzothiophen-3-one are dissolved in 100 ml of 1,2-dichloroethane and the solution is warmed with 7.6 g of thionyl chloride and 1 ml of N,N-dimethylformamide at 60° C. for 2.5 hours and the mixture is then stirred for a further 1 hour at 20°–25° C. The dark red suspension is evaporated under a waterpump vacuum. The resulting brown crystalline product is then heated to the boil in 150 ml of methanol for half an hour. After cooling, the brown-orange crystals are filtered off and these are washed with methanol and subsequently dried at 60° C./100 mm Hg. This gives 6.3 g of crystals which according to the thin layer chromatogram and the IR spectrum are identical to the product described above.

42 g (0.15 mol) of 2-methoxycarbonylchloromethylene-5-methyl[2H]-benzothiophen-3-one are suspended in 700 ml of ethanol and 37.8 g (0.42 mol) of piperidine are added at 20°–25° C. After stirring for three hours at 20°–25° C., the reaction mixture is poured onto 500 g of ice, after which 39.6 g (81.1% of theory) of 2-(α-piperidinomethoxycarbonylmethylene)-5-methyl[2H-]benzothiophen-3-one of the formula

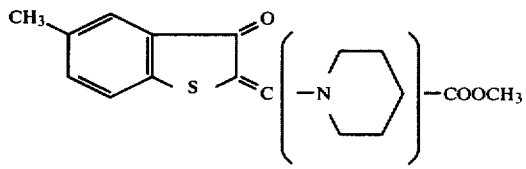

in the form of brownish crystals are filtered off. Recrystallisation from ethyl acetate gives 32.1 g (65.8% of theory) of orange-yellow crystals (melting point 118°–120° C.) of 2-(α-piperidinomethoxycarbonylmethylene)-5-methyl[2H]benzothiophen-3-one.

2-(α-Piperidinomethoxycarbonylmethylene)-6-methyl[2H]-benzothiophen-3-one having a melting point of 153°–155° C. is obtained in an analogous manner by reacting 2-methoxycarbonylchloromethylene-6-methyl-[2H]-benzothiophen-3-one with piperidine.

20.6 g (0.065 mol) of the 2-(α-piperidinomethoxycarbonylmethylene)-5-methyl[2H]benzothiophen-3-one described above in 325 ml of 5% strength sulphuric acid are refluxed for one hour. After cooling, the resulting yellow crystals are filtered off with suction and dried at 60° C./100 mm Hg. This gives 15.5 g (95.7% of theory) of methyl 3-hydroxy-5-methyl[2H]benzothienyl-2-glyoxylate of the formula

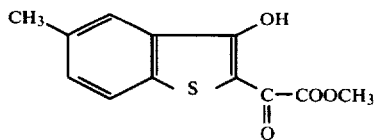

Recrystallisation from 10% strength methanolic sulphuric acid gives yellow crystals having a melting point of 153°–154° C.

The following compounds can be prepared in an analogous manner: methyl 3-hydroxy-6-methyl[2H-]benzothienyl-2-glyoxylate; melting point after recrystallisation from ethyl acetate 147°–149° C., starting from 2-methoxycarbonyl-chloromethylene-6-methyl[2H-]benzothiophen-3-one via 2-(α-piperidinomethoxycarbonylmethylene)-6-methyl[2H]benzothiophen-3-one; and methyl 3-hydroxy-5,6-trimethylene-benzothienyl-2-glyoxylate (melting point 206°–208° C., recrystallised from methyl acetate), starting from 2-methoxycarbonyl-chloromethylene-5,6-trimethylene-[2H]-benzothiophen-3-one by treatment with pyridine and then with 10% strength sulphuric acid.

EXAMPLE 15

The reaction of 2-chlorocarboxymethylene-5,6-trimethylene-benzothiophen-3-one with piperidine and subsequent treatment of the reaction product with 10% strength sulphuric acid gives 3-hydroxy-5,6-trimethylene-benzothienyl-2-glyoxylic acid; melting point after recrystallisation from dilute sodium hydroxide solution, 220°–223° C. (decomposition).

Use Examples (A) Tablets containing 0.1 g of active compound, for example methyl 3-hydroxy-5-methyl[2H]benzothienyl-2-glyoxylate, are prepared as follows:

| Composition: (for 1,000 tablets) | |
|---|---|
| active compound | 100.00 g |
| lactose | 50.00 g |
| wheat starch | 73.00 g |
| colloidal silica | 13.00 g |
| magnesium stearate | 2.00 g |
| talc | 12.00 g |
| water | q.s. |

The active compound is mixed with a portion of the wheat starch and with the lactose and the colloidal silica and the mixture is forced through a sieve. A further portion of the wheat starch is mixed to a paste with five times the amount of water on a waterbath and the above powder mixture is kneaded with this paste until a slightly plastic mass has formed. The plastic mass is pressed through a sieve of about 3 mm mesh width and dried and the dry granules are again forced through a sieve. The remaining wheat starch, the talc and the magnesium stearate are then mixed in and the resulting mixture is pressed to give tablets of 0.25 g. (B) An approximately 2% strength aqueous solution, which is suitable for inhalation, of an active compound which is water-soluble in the free form or in the form of the sodium salt can be prepared, for example, in the following composition:

| Composition: | |
|---|---|
| active compound, for example the sodium salt of methyl 3-hydroxy-5-methyl[2H]benzothienyl-2-glyoxylate | 2,000 mg |
| stabiliser, for example the disodium salt of ethylenediaminetetraacetic acid | 10 mg |
| preservative, for example benzalkonium chloride | 10 mg |
| water, freshly distilled | to make up to 100 ml |

The active compound is dissolved in freshly distilled water with the addition of the equimolar amount of 2 N sodium hydroxide solution. The stabiliser and the preservative are then added. After all of the components have dissolved completely, the resulting solution is made up to 100 ml and filled into small bottles and these are sealed gas-tight.

What is claimed is:

1. A compound of the formula I

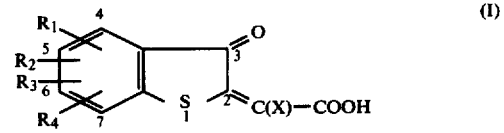

in which X is chlorine, bromine or fluorine, two of $R_1$ to $R_4$ independently of one another are hydrogen or lower alkyl, one of $R_1$ to $R_4$ is hydrogen, a halogen atom, hydroxyl or lower alkyl, and the last of $R_1$ to $R_4$ is hydrogen, a halogen atom, hydroxyl, carboxyl, lower alkyl, lower alkoxy, phenoxy, cycloalkyl of 5 to 8 carbon atoms, benzoyl; benzoyl substituted with alkyl of 1 to 4 carbon atoms, with alkoxy of 1 to 4 carbon atoms or with halogen; alkanoyl of 2 to 7 carbon atoms, amino, -$NQ_1Q_2$ or -$NHCOQ_3$; wherein $Q_1$ is hydrogen or lower alkyl, $Q_2$ is lower alkyl; or $Q_1$ and $Q_2$ together are alkylene of 4 to 7 carbon atoms, thiaalkylene of 4 to 7 carbon atoms, oxaalkylene of 4 to 7 carbon atoms or iminoalkylene of 4 to 7 carbon atoms where the imino group -$NQ_4$ has $Q_4$ as hydrogen or lower alkyl, and $Q_3$ is lower alkyl; or if two of $R_1$ to $R_4$ are hydrogen, the remaining two of $R_1$ to $R_4$ together are alkylene of 3 to 5 carbon atoms, which may be substituted by alkyl of 1 to 4 carbon atoms, which together with the bonding C atoms in the ortho-position form a cycloalkyl group having 5 to 7 ring members which may be substituted by alkyl of 1 to 4 carbon atoms; or together are 1,4-butadienyl which together with the bonding C atoms in the ortho position form a fused benzene ring.

2. A compound of the formula I according to claim 1, in which X is chlorine, $R_1$ and $R_2$ independently of one another are hydrogen or an alkyl group having 1–4 carbon atoms, $R_3$ is hydrogen, chlorine, fluorine, bromine or an alkyl group having 1–4 carbon atoms and $R_4$ is hydrogen, chlorine, fluorine, bromine, —OH, —COOH, cyclohexyl, an alkyl or alkoxy group having 1–4 carbon atoms, an alkanoyl group having 2–7 carbon atoms, an alkanoylamino group having 2–4 carbon atoms or a N,N-dialkylamino group having 1 to 2 carbon atoms in each alkyl part.

3. A compound of the formula I according to claim 1, in which X is chlorine, $R_3$ and $R_4$ are hydrogen and $R_1$ and $R_2$ together form an alkylene group having 3–5 carbon atoms, which is bonded in the 5,6-position, or a 1,4-butadienyl group bonded in the 4,5-position.

4. A compound according to claim 1 of the formula Ia

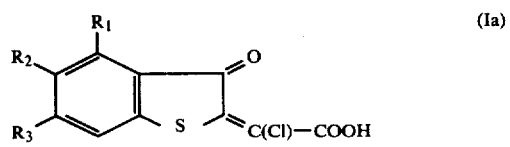

in which $R_1$ and $R_2$ independently of one another are hydrogen or alkyl having 1–4 carbon atoms and $R_3$ is hydrogen, alkyl or alkoxy having 1–4 carbon atoms or —OH, or in which $R_1$ and $R_2$ together form 1,4-butadienyl and $R_3$ is hydrogen, or $R_1$ is hydrogen and $R_2$ and $R_3$ together form alkylene having 3 or 4 carbon atoms.

5. A compound of the formula Ia according to claim 4, in which $R_1$ is hydrogen or methyl and one of the radicals $R_2$ and $R_3$ is methyl and the other is hydrogen or methyl, or in which $R_1$ is hydrogen and $R_2$ and $R_3$ together are trimethylene.

6. A process for the preparation of a compound of the formula I according to claim 1, wherein a compound of the formula II

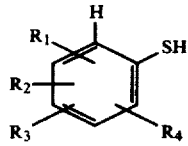
(II)

is reacted with a compound of the formula III

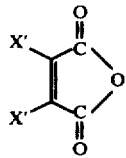
(III)

to give a compound of the formula IV

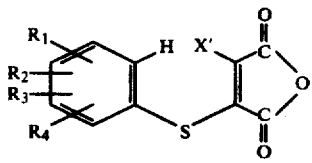
(IV)

in which formulae $R_1$, $R_2$, $R_3$ and $R_4$ are as defined under formula I and the two X' in formula III and IV independently of one another are chlorine, fluorine or bromine, and the compound of the formula IV is subsequently converted in the presence of a Lewis acid to a compound of the formula I.

7. A process according to claim 6, wherein dichloromaleic anhydride is used as the compound of the formula III.

8. A compound according to claim 1 of the formula

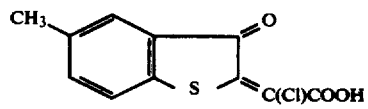

9. A compound according to claim 1 of the formula

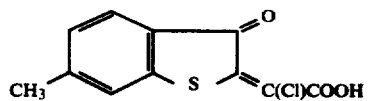

10. A compound according to claim 1 of the formula

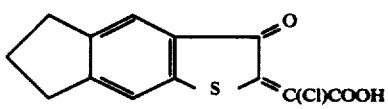

* * * * *